(12) United States Patent
Brown

(10) Patent No.: US 6,468,976 B1
(45) Date of Patent: Oct. 22, 2002

(54) MONOHYDRATE LISINOPRIL

(75) Inventor: John Brown, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/950,472

(22) Filed: Sep. 10, 2001

(51) Int. Cl.$^7$ ............................................. C07K 5/087
(52) U.S. Cl. ........................ 514/18; 514/19; 530/331; 424/464; 424/469
(58) Field of Search ................... 514/18, 19; 530/331; 424/464, 489

(56) References Cited

FOREIGN PATENT DOCUMENTS

WO          00/69417     * 11/2000

OTHER PUBLICATIONS

Bernstein, Joel Angew. Chem., Int. Ed. 38(23), 3441–3461, 1999.*
Bugay, David E. J. Pharm. Biomed. Anal. (1996), 15(1), 49–61.*
Hancock, Bruno C., Pharm. Res. (1994), 11(4), 471–7.*
Hancock, Bruno C. J. Pharm. Sci. (1997), 86(1), 1–12.*
Harris, Kenneth D. M. Angew. Chem., Int. Ed. (2001), 40(9), 1626–1651.*
McCauley, J. A., J. Phys. D: Appl. Phys. (1993), 26(8B), B85–B89.*
Nordhoff, S. J. Therm. Anal. Calorim. (1999), 57(1), 181–192.*
Surana, Rahul, Powder Diffr. (2000 ), 15(1), 2–6.*
Wu J Pharm Sci 74, 352, 1985.*
Ip et al., 1992, "Lisinopril", *Analytical Profiles Of Drug Substances And Excipients* vol. 21 (Academic Press) pp 233–276.
Wang et al., 2000, "Thermal–Dependent Dehydration Process and Intramolecular Cyclization of Lisinopril Dihydrate in the Solid State", Chem. Pharm. Bull. 48:1890–1893.

* cited by examiner

*Primary Examiner*—Christopher S. F. Low
*Assistant Examiner*—David Lukton
(74) *Attorney, Agent, or Firm*—Ropes & Gray

(57) ABSTRACT

The present invention relates to a novel monohydrate form of 1-(N$^2$-[(S)-1-carboxy-3-phenylpropyl]-L-lysyl)-L-proline known under the generic name lisinopril. Further, the present invention also relates to the use of the novel monohydrate form of lisinopril for the treatment of hypertension and other cardiovascular diseases, pharmaceutical compositions containing it as well as processes for the preparation of the novel monohydrate form of lisinopril.

14 Claims, 3 Drawing Sheets

MONOHYDRATE LISINOPRIL

BACKGROUND OF THE INVENTION

The compound 1-($N^2$-[(S)-1-carboxy-3-phenylpropyl]-L-lysyl)-L-proline, having the generic name lisinopril, as well as therapeutically acceptable salts thereof, are described in U.S. Pat. Ser. No. 4,374,829 (Merck & Co. Inc.), incorporated herein by reference. In said patent the compound is described in Example 119, and is referred to as N-α-[1(S)-1-carboxy-3-phenylpropyl]-L-lysyl]-L-proline. The divisional application to this patent, which has resulted in U.S. Pat. No. 4,472,380, incorporated herein by reference, claims pharmaceutical compositions that include lisinopril pharmaceutical compositions. Lisinopril is a drug on which extensive clinical experience has been obtained. It is currently sold under the trademark ZESTRIL® or PRINIVIL®.

Lisinopril is a peptidyl dipeptidase inhibitor useful in treating cardiovascular diseases and disorders, such as hypertension and congestive heart failure (CHF) in mammals and especially in man. It inhibits the angiotensin converting enzyme (ACE) that catalyses the conversion of angiotensin I to the vasoconstrictor peptide, angiotensin II. Angiotensin II also stimulates aldosterone secretion by the adrenal cortex. Inhibition of ACE results in decreased concentrations of angiotensin II which results in decreased vasopressor activity and reduced aldosterone secretion.

ACE is known to be present in the endothelium and increased ACE activity in diabetic patients which results in the formation of angiotensin II and destruction of bradykinin, potentiates the damage to the endothelium caused by hyperglycaemia. ACE inhibitors, including lisinopril, inhibit the formation of angiotensin II and breakdown of bradykinin and hence ameliorate endothelial dysfunction.

In terms of the pharmacokinetic properties of lisinopril, following oral administration, peak serum concentrations occur within about 7 hours, although there is a trend to a small delay in time taken to reach peak serum concentrations in acute myocardial infarction patients. On multiple dosing lisinopril has an effective half-life of accumulation of about 12.6 hours. Declining serum concentrations exhibit a prolonged terminal phase, which does not contribute to drug accumulation. This terminal phase probably represents saturable binding to ACE and is not proportional to dose. Based on urinary recovery, the mean extent of absorption of lisinopril is approximately 25%, with interpatient variability (6–60%) at all doses tested (5–80 mg). Lisinopril does not undergo metabolism and absorbed drug is excreted unchanged entirely in the urine.

The monohydrate form of lisinopril of the present invention, (herein "monohydrate lisinopril form 2") is different from the monohydrate form of lisinopril ("monohydrate lisinopril form 1") previously reported by Ip et al., (*Lisinopril*, in Analytical Profiles of Drug Substances and Excipients (Ed., Brittain, H. G.), Academic Press, Volume 21, pp 233–276, 1992). The only characterising data of the monohydrate in this publication is an X-ray powder diffraction (XRPD) pattern shown as a plot of intensity of diffracted x-rays vs °2θ (FIG. 12, p257). No other analytical data or description of the monohydrate is given, nor is its preparation described. Despite this lack of teaching of how to make the monohydrate of Ip et al., the inventors have managed not only to prepare the new monohydrate (denoted monohydrate lisinopril form 2) of the present invention, but also what is believed to be the monohydrate disclosed by Ip et al., (denoted monohydrate lisinopril form 1).

Monohydrate lisinopril form 2 is also different from the "monohydrate" that is disclosed in Wang, S-L. et al., 2000, Chem. Pharm. Bull. 48, 1890–93. Wang et al. describes the generation of a lisinopril "monohydrate" by heating lisinopril dihydrate until weight loss corresponding to one mole of $H_2O$ per mole of lisinopril was observed. The present inventors have performed the identical experiment as Wang et al. and have found that the resulting "monohydrate" is strongly hygroscopic, i.e., the evolved water is quickly reabsorbed from the atmospheric water when the crystals are returned to room temperature. By contrast, both form 1 and form 2 monohydrates of the invention are stable at a standard room temperature and humidity.

The monohydrate lisinopril form 2 of the present invention is substantially more soluble than the dihydrate of lisinopril (Zestril), and in view of this increased solubility, it may prove more suitable for the preparation of a 'fast melt' tablet formulation than conventional lisinopril dihydrate.

SUMMARY OF THE INVENTION

The present invention relates to a novel monohydrate form of 1-($N^2$-[(S)-1-carboxy-3-phenylpropyl]-L-lysyl)-L-proline. 1-($N^2$-[(S)-1-carboxy-3-phenylpropyl]-L-lysyl)-L-proline is known under the generic name lisinopril and its novel monohydrate form is hereinafter referred to as monohydrate lisinopril form 2. The present invention further relates to the use of monohydrate lisinopril form 2 in medical treatments, pharmaceutical compositions comprising monohydrate lisinopril form 2, in particular 'fast melt' formulations, and processes for the preparation of monohydrate lisinopril.

Monohydrate lisinopril form 2 can be characterized by several different criteria. By one criterion, monohydrate lisinopril form 2 is the crystal form of lisinopril that results from the precipitation of lisinopril by the process of dissolving any form of lisinopril in water, forming a crystalline precipitate by the addition of excess isobutanol and drying the precipitate that has been formed at a temperature of not more than 80° C. By another criterion, monohydrate lisinopril form 2 is the crystalline form of lisinopril that is characterized as having an XRPD pattern that has strong or very strong peaks at 2-d spacings of 12.0 and 11.5Å. Additional criterion for the identification of monohydrate lisinopril from 2 are set forth in the detailed description of the invention. Such criteria include: further characterisations of the XRPD pattern; temperature of the onset of melting and temperature of the peak of the endotherm; a characteristic infrared (IR) absorption spectrum; and a characteristic Raman spectrum.

BRIEF DESCRIPTION OF THE DRAWINGS

The invention is further illustrated, but in no way limited, by the following examples and figures in which.

DETAILED DESCRIPTION OF THE INVENTION

Figure 1:
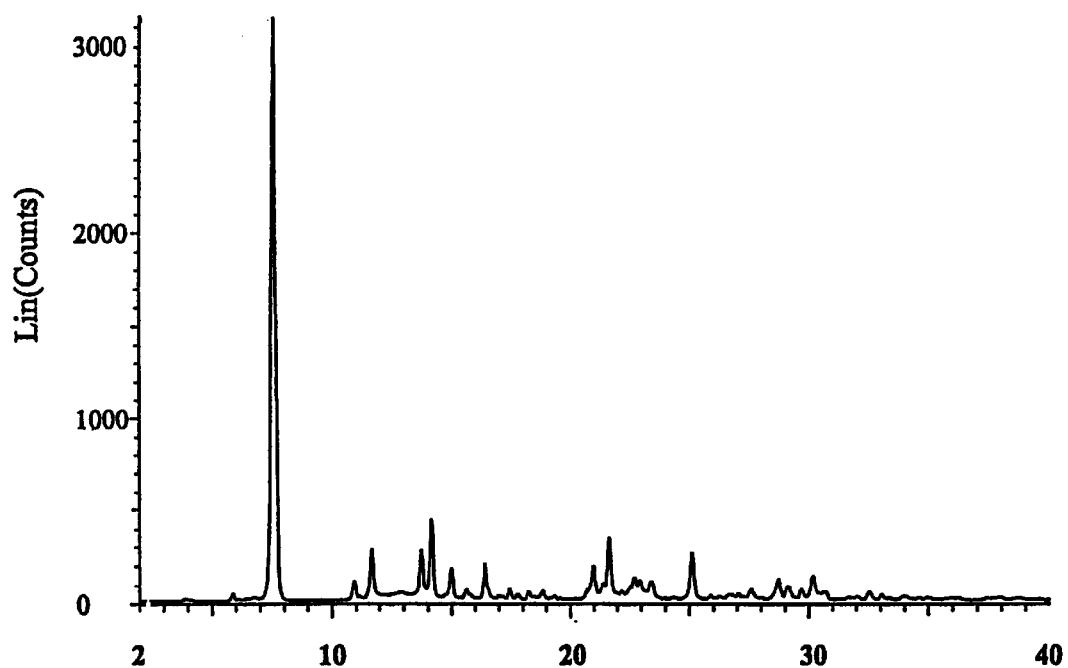
FIG. 1 is an X-ray powder diffractogram (XRPD) of monohydrate lisinopril form 1.

It has surprisingly been found that the lisinopril can be prepared in a novel monohydrate form, hereafter "monohydrate lisinopril form 2." Moreover, it has been found that monohydrate lisinopril form 2 possesses far greater solubility than lisinopril dihydrate (which is itself also crystalline). The more soluble monohydrate lisinopril form 2 is more suitable to certain formulations where quick solubility is desired, such as 'fast melt' (melt-on-the-tongue type) formulations. It is an object of the present invention to provide monohydrate lisinopril form 2. It is a further object of the invention to provide mixtures of monohydrate lisinopril form 2 with other solid forms of lisinopril, such as lisinopril dihydrate. Another object of the present invention is to provide a process for the preparation of monohydrate lisinopril form 2, substantially free from other forms of lisinopril. Additionally it is an object of the present invention to provide pharmaceutical formulations comprising monohydrate lisinopril form 2.

Monohydrate lisinopril form 2 is a crystalline form exhibiting advantageous properties, such as being more soluble than crystalline lisinopril dihydrate. In addition, the novel monohydrate lisinopril form 2 particles are smaller and in a narrower size range (typically 5 μm or less in edge length) than the dihydrate crystals. The more regular size and shape of the monohydrate lisinopril form 2 particles is expected to impart improved flow characteristics and so aid tablet manufacture compared to the long needle-like structures of lisinopril dihydrate. In addition, the use of a form of lisinopril having a reproducible particle size distribution may obviate the need for milling prior to capsulation or tabletting. ZESTRIL® is conventionally manufactured using milling, wet granulation and tabletting. Obviating the need for a milling step could speed up manufacture and reduce costs.

Tablet manufacture by direct compression, as opposed to wet granulation, is prone to size-based segregation of the drug substance from the remaining excipients, leading to a non-uniform mix and to tablets of variable drug content. Segregation is exacerbated by large differences in the particle size of the drug substance and the excipients. The more regular particle size of the monohydrate lisinopril form 2 compared to the dihydrate material would be expected to be prone to less segregation.

Thus, according to a first aspect of the invention there is provided monohydrate lisinopril form 2 characterized in having strong or very strong X-ray diffraction peaks at d-spacings of about 12.0 and 11.5 and additionally characterized by diffraction peaks at 7.6, 6.5, 5.4, 4.59, 4.23, 4.16, 4.09, and 3.91Å. The XRPD pattern of monohydrate lisinopril form 2 is further characterized by the lack of X-ray diffraction peaks at d-spacings of about 15.2, 8.1, 6.3, 5.69 and 4.72Å, which are present in the XRPD pattern of monohydrate lisinopril form 1 disclosed by Ip et al.

Monohydrate lisinopril form 2 can also be identified by the criterion that melt onset occurs at about 167° C. and the peak of the endotherm occurs at about 177° C. when measured by DSC at a heating rate of 10° C./min in a pierced pan in air.

Monohydrate lisinopril form 2 can also be identified by an IR absorption spectrum having bands at about 3637, 3440, 1648, 1617, 1564, 1451, 1443, 1373, 1205, 759 and 705 cm$^{-1}$, and the absence of absorption bands at about 3407 and 3293 cm$^{-1}$.

Monohydrate lisinopril form 2 can also be identified by a Raman spectrum having bands at about 3061, 3050, 3042, 2988, 2937, 2900, 1651, 1600, 1580, 1375, 1196, 1001 and 834 cm$^{1}$, and the absence of bands at about 3070, 2966, 2870, 1604 and 1585 cm$^{-1}$.

Figure 2:
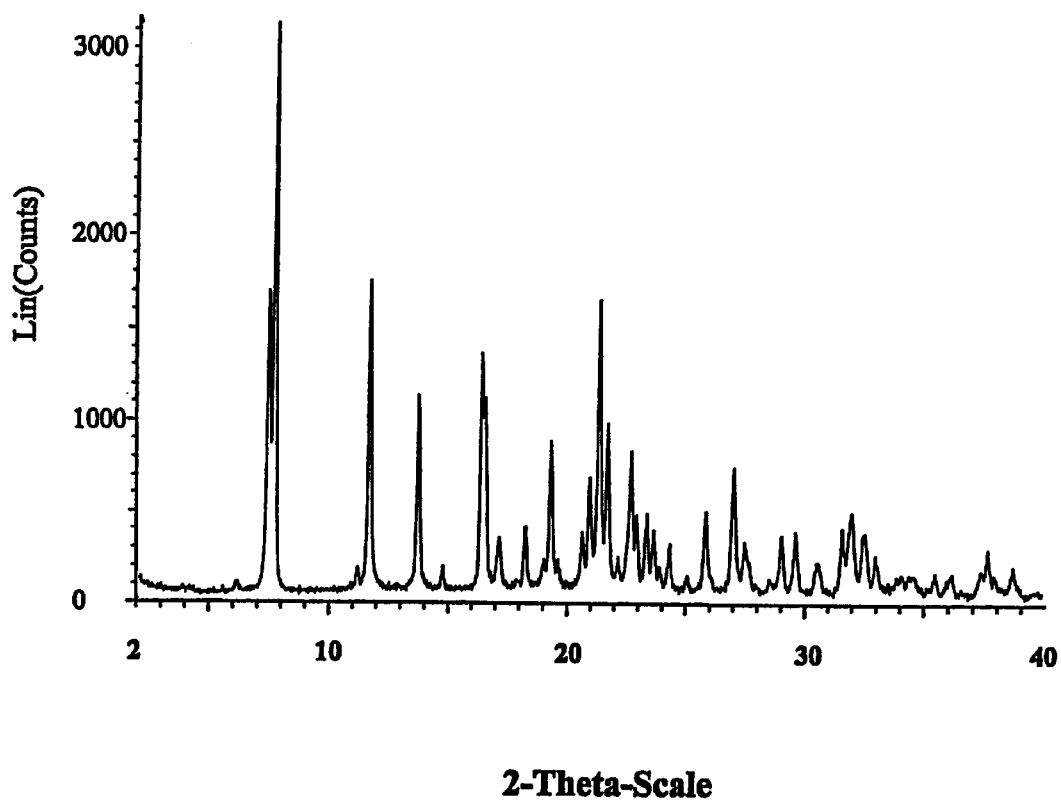
FIG. 2 is an X-ray powder diffractogram (XRPD) of monohydrate lisinopril form 2.

One routine method of differentiating monohydrate lisinopril from 2 from other crystalline and non-crystalline forms of lisinopril is X-ray powder diffraction (XRPD). The XRPD pattern of monohydrate lisinopril form 2, as illustrated in FIG. 2 and with reference to Table 2, can be seen to exhibit additional intensity on some peaks, but also to lack a number of peaks found in the monohydrate disclosed in Ip et al. In the first instance, a monohydrate lisinopril, either of form 1 or form 2, can be differentiated from lisinopril dihydrate, or mixtures of monohydrate and dihydrate lisinopril, by determining the water content. A lisinopril monohydrate contains 4.08%, by weight, of water while lisinopril dihydrate contains 8.16%, by weight, of water. Standard methods of determination of water content are Karl-Fischer titration and Thermogravimetric Analysis (TGA).

The various physicochemical properties of the monohydrate lisinopril form 2 were identified according to the methods employed in the Examples. It should be understood that these are experimental values and spectrums, which are provided for reference purposes. Whether or not a particular compound is monohydrate lisinopril form 2, should not be determined according to the precise values determined in the Examples. It will be readily understood by those skilled in the art that such experimental values and spectrums may involve experimental errors due to factors including the measuring apparatus, the process, experimental conditions etc. The various techniques identified and approximate figures listed are however sufficient to enable the person skilled in the art to determine whether or not a particular compound is monohydrate lisinopril form 2 according to the present invention.

Monohydrate lisinopril form 2, or the presence of some monohydrate lisinopril form 2, can be distinguished from other crystalline and non-crystalline forms of lisinopril, using X-ray powder diffraction, Raman spectroscopy, differential scanning calorimetry, solid state nuclear magnetic resonance spectra (ssNMR) or infra-red spectroscopy. Each of these techniques is well established in the art. Furthermore, monohydrate lisinopril form 2 is much more soluble than crystalline lisinopril dihydrate, providing another means of discriminating between the dihydrate and monohydrate lisinopril forms, or detecting an amount of monohydrate lisinopril form 2 within a lisinopril dihydrate preparation.

As noted above, a routine method of differentiating monohydrate lisinopril form 2 from other crystalline and non-crystalline forms of lisinopril is X-ray powder diffraction (XRPD), optionally combined with analysis of water content.

Another method of distinguishing physical forms, such as dihydrate lisinopril and monohydrate lisinopril form 2, is $^{13}$C solid state NMR spectra (ssNMR) acquired with cross polarization, magic angle spinning and high power proton decoupling. The isotropic chemical shifts (peak positions) measured in solid-state NMR spectra are not only a function of the molecule's atomic connectivity, but also of molecular conformation and inter- and intra-molecular interactions. Thus different peak positions may be observed for different physical forms.

In one embodiment of the invention, monohydrate lisinopril form 2 is substantially free from other forms of lisinopril. Substantially free from other forms of lisinopril shall be understood to mean that the composition comprising monohydrate lisinopril form 2 contains less than 50%, preferably less than 25%, more preferably less than 10% and still more preferably less than 5% of any other forms of lisinopril, e.g. dihydrate lisinopril or amorphous lisinopril.

In a further embodiment monohydrate lisinopril form 2 is in increasing order of preference, at least 70%, 80%, 85%, 90%, 95%, 97%, 98%, 99% and 100% pure. The presence of organic contaminants can be detected by HPLC. Purity can be measured using a solid-state method such as XRPD or ssNMR.

It will be appreciated however, that because of the enhanced solubility property of monohydrate lisinopril form 2, mixtures comprising substantially dihydrate or other solid forms of lisinopril with monohydrate lisinopril, depending on the amount of form 2 monohydrate product present, may also possess varying degrees of increased solubility. Such mixtures comprising monohydrate lisinopril can be prepared, for example, by mixing monohydrate lisinopril form 2 prepared according to the present invention with other solid forms of lisinopril, such as crystalline dihydrate form, prepared according to prior art methods. A mixture might also be prepared if the manufacturing process is incomplete, or incorporates steps that allow or cause monohydrate product to be formed.

Thus, the present invention also relates to mixtures comprising monohydrate lisinopril form 2 in admixture with other solid forms of lisinopril. Such mixtures comprising monohydrate lisinopril form 2 include for instance mixtures containing a detectable amount of monohydrate lisinopril form 2, which is 1%, 2%, 5%, 10%, 20%, 30%, 40%, 50%, 60%, 70% 80%, 90%, 95%, 98% or 99% (by weight), of the total lisinopril.

Examples of other solid forms of lisinopril include, but are not limited to, dihydrate lisinopril and monohydrate lisinopril form 1.

A detectable amount of monohydrate lisinopril form 2 is an amount that can be detected using conventional techniques, such as FT-IR, Raman spectroscopy, XRPD, TGA, DSC and the like.

Numerous techniques can be employed to detect a particular form of a compound within a mixture. The limits of detection of a particular form in a mixture with another form, e.g., monohydrate form 2 mixed with dihydrate, is as follows: by XRPD it is reported to be approximately 5% according to Hancock and Zografi (J. Pharm. Sci., 86:1–12, 1997) and approximately 2% according to Surana and Suryanarayanan (Powder Diffraction, 15:2–6, 2000). The limits of detection by solution calorimetry is reported to be approximately 1% according Hogan and Buckton (International Journal of Pharmaceutics, 207:57–64, 2000). The limits of detection by solid state NMR is reported to be approximately 5–10% according to Saindonet al., (Pharmaceutical Research, 10:197–203, 1993). The limits of detection by near infra red spectroscopy is reported to be approximately 2–5% according to Blanco and Villar (Analyst, 125:2311–2314, 2000). The limits of detection by Modulated Differential Scanning Calorimetry (MDSC) is reported to be approximately 6% according to Saklatvala et al., (International Journal of Pharmaceutics, 192: 55–62, 1999). The limits of detection by FT-Raman spectroscopy is reported to be approximately 2% according to Taylor and Zografi (Pharm. Res. 15:755–761, 1998).

Monohydrate lisinopril generically can be prepared by crystallization from alcohol solutions. A suitable method for preparing monohydrate lisinopril form 2 is to dissolve crystalline lisinopril dihydrate, or any other form of lisinopril in water and add an organic water miscible solvent, such as isobutanol, followed by precipitation, filtration and drying.

According to one aspect of the invention there is provided a process for the preparation of monohydrate lisinopril form 2 comprising the steps of:

a) dissolving lisinopril of any form, or a mixture of forms of lisinopril in a aqueous solvent;
b) adding a water miscible organic solvent, such as isobutanol;
c) allowing a precipitate to form; and,
d) isolating and drying the precipitate.

According to one aspect of the invention there is provided a process for the preparation of monohydrate lisinopril fcomprising the steps of:

a) dissolving lisinopril of any form, or a mixture of lisinopril of any form in water;
b) adding isobutanol;
c) maintaining the product of (b) in a condition under in crystalline lisinopril forms and isolating the crystals; and,
d) drying the crystals of (c), preferably under vacuum at approximately 80° C.

By the term 'any form' we include, solvated and desolvated forms, crystalline forms and other non-crystalline forms.

Mixing, e.g. agitation or stirring, is preferable during both the dissolving step and the precipitation step. The precipitation should continue for a period to ensure that monohydrate product formation is as complete as possible, e.g. up to 15 hours, preferably, 1–8 hours.

The product may be separated from the solution, e.g. by filtration or centrifugation. The product can be dried to a constant weight, e.g. at 80° C., and preferably at reduced pressure, for, e.g. 10 to 48 hours. For storage, the monohydrate product is preferably kept at 25° C., 60% RH (ambient conditions).

In a further aspect, the invention provides a compound obtainable by a process or method as described above.

'Zestril' has received regulatory approval for use in the following indications:

Hypertension 'Zestril' is indicated in the treatment of essential hypertension and in renovascular hypertension. It may be used alone or concomitantly with other classes of antihypertensive agents.

Congestive Heart Failure 'Zestril' is indicated in the management of congestive heart failure as an adjunctive treatment with diuretics and, where appropriate, digitalis. High doses reduce the risk of the combined outcomes of mortality and hospitalization.

Acute Myocardial Infarction 'Zestril' is indicated for the treatment of haemodynamically stable patients within 24 hours of an acute myocardial infarction, to prevent the subsequent development of left ventricular dysfunction or heart failure and to improve survival. Patients should receive, as appropriate, the standard recommended treatments such as thrombolytics, aspirin and beta-blockers.

Renal And Retinal Complications of Diabetes Mellitus In normotensive insulin-dependent and hypertensive non-insulin-dependent diabetes mellitus patients who have incipient nephropathy characterised by microalbuminuria, 'Zestril' reduces urinary albumin excretion rate. 'Zestril' reduces the risk of progression of retinopathy in normotensive insulin-dependent diabetes mellitus patients.

According to the invention there is further provided a pharmaceutical composition comprising monohydrate lisinopril form 2, as active ingredient, in association with a pharmaceutically acceptable carrier, diluent or excipient and optionally other therapeutic ingredients. Compositions comprising other therapeutic ingredients are especially of interest in the treatment of hypertension, congestive heart failure, acute myocardial infarction and in renal and retinal complications of diabetes mellitus.

The invention also provides the use of monohydrate lisinopril form 2 in the manufacture of a medicament for use in the treatment of a cardiovascular related condition, and in particular, a method of treating a hypertensive or congestive heart failure condition which method comprises administering the medicament to a subject suffering from said condition a therapeutically effective amount of lisinopril.

The invention also provides the use of monohydrate lisinopril form 2 in treating hypertension, congestive heart failure, acute myocardial infarction and in renal and retinal complications of diabetes mellitus.

Any suitable route of administration may be employed for providing the patient with an effective dosage of drug comprising monohydrate lisinopril form 2 according to the invention. For example, peroral or parenteral formulations and the like may be employed. Dosage forms include capsules, tablets, dispersions, suspensions and the like, e.g. enteric-coated capsules and/or tablets, capsules and/or tablets containing enteric-coated pellets of lisinopril. In all dosage forms monohydrate lisinopril can be mixed or combined with other suitable constituents. One preferred route of administration is peroral using fast melt tablets.

The compositions of the invention comprise the compound of the invention. The compositions may be conveniently presented in unit dosage forms, and prepared by any methods known in the art of pharmacy.

In view of the enhanced solubility that monohydrate lisinopril form 2 has compared to crystalline lisinopril dihydrate, compositions wherein some, but preferably a substantial amount, of the total amount of the lisinopril is monohydrate (i.e.>20%), can be prepared as a 'fast melt' tablet and/or formulation.

A fast melt tablet is defined as a tablet dosage form that is intended to disintegrate in the patient's mouth without the need for chewing or water. In one embodiment, the fast melt tablet disintegrates in approximately one minute. If the drug and tablet excipients are sufficiently soluble, the fast melt tablet dissolves to a complete solution before the patient swallows.

Several advantages of fast melt tablets over conventional oral tablets and liquids may exist. Patient compliance may improve because of ease of swallowing, lack of need for water, and taste-masking and improved accuracy of dosage. Patient populations that may benefit the most include geriatric patients, pediatric patients and patient who cannot swallow or have difficulty in swallowing. A fast melt tablet would also benefit patients with congestive heart failure who tend to retain fluid, and therefore are treated with fluid intake restriction. The fluid used to take their medications are included in the amount of fluid that they are prescribed per day (which may be as little as 500 ml), so a fast melt tablet that can be taken without fluid would benefit these patients.

Fast melt tablets are manufactured by a variety of tablet technologies including wet granulation, direct compression and freeze-drying (see for example: Corveleyn and Remon, International Journal of Pharmaceutics, (1997) 152: 215–225).

For a general review on fast melt technology please consult, Habib et al., (Critical Reviews in Therapeutic Drug Carrier Systems, 17(1):61–72, 2000).

According to a further aspect of the invention there is provided a fast melt tablet formulation comprising monohydrate lisinopril form 2.

Crystalline lisinopril dihydrate is soluble in water and goes into solution in the gastrointestinal tract rapidly after ingestion. This is demonstrated by the dissolution of the current marketed Zestril® tablets in which typically greater than 90% of the dose is dissolved within 15 minutes. Once in solution, absorption is limited by the physicochemical characteristics of the compound, its ability to cross the gastrointestinal mucosa and enter into the blood stream and transit time of the gut. A form that would go into solution more rapidly would only affect the first step, however. Thus, despite the enhanced solubility that a lisinopril formulation comprising monohydrate lisinopril form 2 would be expected to have, because solubility is not a limiting step in the rate and extent of absorption of lisinopril, it is unexpected that this would affect the bio-availability or the clinical benefits of lisinopril.

In the practice of the invention, the most suitable route of administration as well as the magnitude of a therapeutic dose of monohydrate lisinopril form 2 in any given case will depend on the nature and severity of the disease to be treated. The dose, and dose frequency, may also vary according to the age, body weight, and response of the individual patient.

In general, a suitable oral dosage form may cover a dose range from 0.5 mg to 150 mg total daily dose, administered in one single dose or in multiple, such as, equally divided doses. A preferred dosage range is from 1 mg to 60 mg.

Combination therapies comprising monohydrate lisinopril form 2 and other active ingredients in separate dosage forms, or in one fixed dosage form, may also be used. Examples of such active ingredients include anti-bacterial compounds, non-steroidal anti-inflammatory agents, antacid agents, alginates, prokinetic agents, other antihypertensive agents, diuretics, digitalis, thrombolytics, aspirin and beta-blockers.

EXAMPLES

Example 1

Preparation of Forms of Lisinopril

Preparation 1

Crystalline lisinopril dihydrate (10 g), prepared according to standard methodology, e.g., Ip et al., Lisinopril supra., was dissolved in 250 ml methanol in a suitable vessel and heated briefly to reflux (60–65° C.). The solution was then filtered to remove any undissolved lisinopril and left to crystallize through self-cooling. The crystals formed (preparation 1) were then isolated by filtration.

Preparation 2

Crystalline lisinopril dihydrate (5 g), prepared according as above, was dissolved in 50 ml water and then heated to about 45 ° C. until the volume of solvent (water) was reduced to about 10 ml. 200 ml isobutanol was then added and the resulting mixture was stirred overnight. The crystals formed were isolated by filtration and dried at 80° C. for two days.

Preparation 3

Crystalline lisinopril dihydrate, prepared as above, was heated until an approximately 4.2% weight loss was observed, corresponding to the loss of 1 mole of $H_2O$ per mole of lisinopril. The partially dehydrated material was allowed to stand for about 5 hours. Upon thermogravimetric analysis after 5 hours standing at ambient conditions the material was found to have regained the lost weight and to have become a dihydrate. This result showed that the partially dehydrated lisinopril dihydrate is not a stable monohydrate and, hence, does not have the same crystal structure as either the form 1 or form 2 monohydrates, which were observed to be stable under ambient conditions.

Example 2

Characterization of the Monohydrate Forms of Lisinopril using X-ray Powder Diffraction X-ray diffraction analysis was carried out on preparations 1 and 2 according to standard methods, which can be found in e.g. Bunn, C. W. (1948), Chemical Crystallography, Clarendon Press, London; or Klug, H. P. & Alexander, L. E. (1974), X-Ray Diffraction Procedures, John Wiley and Sons, New York.

Figure 3:
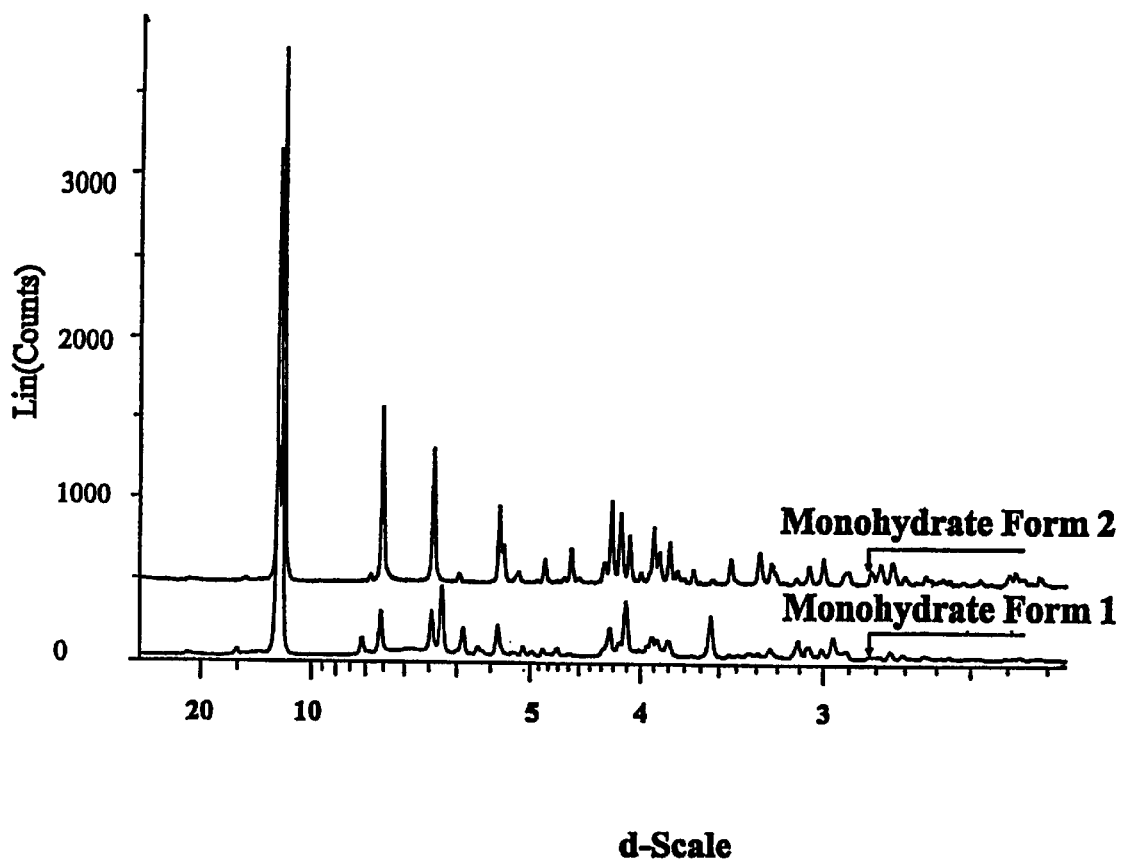
FIG. 3 is an X-ray powder diffractogram (XRPD) of monohydrate lisinopril form 1 overlaid with monohydrate lisinopril form 2.

Both preparations are crystalline and their XRPD patterns are given in FIGS. 1 & 2. For comparison purposes FIG. 3. is an overlay of FIGS. 1 and 2. The XRPD patterns were obtained using CuK$_{\alpha 1/\alpha 2}$ radiation, wavelength 1.5418Å, on a Siemens D5000 diffractometer.

Table of interplanar (d) spacings vs relative intensity are also given in Table 2. The relative intensities are described according to the following definitions:

TABLE 1

| % Relative Intensity | Definition |
| --- | --- |
| 25–100% | vs (very strong) |
| 10–25% | s (strong) |
| 3–10% | m (medium) |
| <3% | w (weak) |

Data for Table 2 were generated using the Siemens Diffracplus software for preparations 1 and 2. In order to obtain such tables for the monohydrate disclosed by Ip et al., the published diffractogram was photoenlarged and peak positions measured manually. Relative intensities could not be calculated since the most intense peak is off-scale in that publication; peak intensities were therefore ranked 1 to 10 for the most intense peaks.

TABLE 2 d-1 data on the three monohydrate lisinoprils

| Monohydrate 1 | | Ip et al., monohydrate | | Monohydrate 2 | |
| --- | --- | --- | --- | --- | --- |
| d-spacing/Å | R.I./% | d-spacing/Å | Rank | d-spacing/Å | R.I./% |
| 15.2 | w | 15.4 | | NPD | |
| ~14.5 | w | ~14.5 | w | 14.5 | w |
| Peak overlap with monohydrate 2 | | | | 12.0 | vs |
| 11.7 | vs | ~11.8 | 1 | Peak overlap with monohydrate 1 | |
| Peak overlap with monohydrate 2 | | | | 11.5 | vs |
| 8.1 | m | 8.1 | — | NPD | |
| ~8.0 | sh | npd | | 7.9 | m |
| 7.6 | m | 7.6 | 2 | 7.6 | vs |
| 6.9 | w (broad) | NPD | | NPD | |
| 6.5 | m | 6.5 | 4 | 6.5 | vs |
| 6.3 | s | 6.3 | 6 | NPD | |
| ≈6.0, sh | | ~6.0 | | 6.0 | w |
| 5.92 | m | 5.92 | — | NPD | |
| 5.69 | w | 5.68 | — | NPD | |
| 5.41 + sh | m | 5.42 | 3 | 5.40 + 5.35 (unresolved) | vs |
| ≈5.2 | w (broad) | 5.19 | | 5.16 | m |
| 5.09 | w | 5.09 | | NPD | |
| 4.99 | w | sh | | NPD | |
| 4.86 | w | 4.86 | | 4.86 | m |
| 4.72 | w | 4.73 | | NPD | |
| NPD | | NPD | | 4.66 | m |
| 4.60 | w | 4.58 | 7 | 4.59 | s |
| NPD | | NPD | | 4.52 | w |
| ≈4.3 sh | | ≈4.3 sh | | 4.29 | m |
| 4.24 | m | 4.23 | 9 | 4.23 | s |
| 4.16 | w | 4.16 | 8 | 4.16 | vs |
| 4.11 | s | 4.10 | 5 | 4.09 | vs |
| 4.01 | w | sh | | 4.00 | m |
| 3.92 | w | 3.91 | | 3.91 | s |
| 3.88 | w | sh on previous peak | | 3.87 | s |
| 3.80 | w | 3.80 | 10 | 3.80 | s |
| NPD | | NPD | | 3.75 | m |
| NPD | | NPD | | 3.71 | w |

TABLE 2-continued d-1 data on the three monohydrate lisinoprils

| Monohydrate 1 | | Ip et al., monohydrate | | Monohydrate 2 | |
| --- | --- | --- | --- | --- | --- |
| d-spacing/Å | R.I./% | d-spacing/Å | Rank | d-spacing/Å | R.I./% |
| 3.66 | w | 3.66 | | 3.65 | m |
| 3.55 | m | 3.54 | | 3.54 | w |
| 3.45 | w | 3.45 | | 3.44 | s |
| 3.33 | w | 3.34 | | NPD | |
| 3.30 | w | 3.30 | | 3.29 | vs |
| 3.23 | w | 3.24 | | 3.23 | m |
| 3.11 | m | 3.11 | | 3.12 | w |
| 3.07 | w | 3.06 | | 3.07 | m |
| 3.01 | w | 3.01 | | 3.01 | m |
| 2.96 | m | 2.96 | | NPD | |
| 2.91 | w | 2.93 | | 2.92 | m |
| 2.82 | w | 2.83 | | 2.82 | w |
| 2.79 | w | 2.80 | | 2.79 | w |
| 2.75 | w | 2.75 | | 2.75 | m |
| 2.71 | w | 2.72 | | 2.71 | m |
| 2.64 | w | 2.63 | | 2.63 | w |

NPD = No Peak Detected
sh = shoulder

The XRPD data on monohydrate form 1 is a very close match for the XRPD disclosed by Ip et al. Of 43 peaks in monohydrate form 1 in the angular range 5–35°2θ, 41 are also present in the monohydrate disclosed by Ip et al. It can therefore be concluded that monohydrate form 1 has the same crystal structure as the monohydrate disclosed by Ip et al.

The XRPD patterns of both monohydrate form 1 and that disclosed by Ip et al., differ from monohydrate form 2 in several key respects, despite many peak overlaps. The most intense peak in the XRPD of monohydrate form 2 occurs at a higher diffraction angle than that of monohydrate form 1. Monohydrate form 2 contains several reflections not seen in the XRPD of monohydrate form 1, including those with d-spacings of 12.0 (which appears as a smaller peak on the low angle side of the most intense reflection), 4.52, 3.75 and 3.71Å. In addition there are several reflections which exhibit much higher intensities in the XRPD of monohydrate form 2 than monohydrate form 1, including those with d-spacings of 5.16, 4.59, 4.16, 3.75, 3.65, 3.44 and 3.29 Å.

Several peaks present in the XRPD patterns of monohydrate form 1 are absent from monohydrate form 2. These correspond to d-spacings of 15.2, 8.1, 6.3, 5.69 and 4.72Å (diffraction angles of 5.8, 10.9, 14.1, 15.6 and 18.8 °2θ respectively). The most obvious of these occurs at a d-spacing of 6.3 Å corresponding to a diffraction angle of 14.1 °2θ in FIGS. 1 to 3.

For the purposes of this application a signal of less than 0.5% relative intensity is not classified as a peak.

Example 3

Characterization of Monohydrate Forms of Lisinopril by DSC, TGA, Raman and IR.

Further characterization of the monohydrates was carried out. This analysis used thermal methods (DSC & TGA), spectroscopy (Raman & IR) and optical and electron microscopy. The solubilities of the monohydrates were also measured.

Differential Scanning Calorimetry (DSC) was performed using a Mettler DSC820 instrument, according to standard methods, for example those described in Höhne et al. (1996) *Differential scanning Calorimetry, Springer*, Berlin.

DSC shows that the monohydrates 1 and 2 have different melting points when measured by onset or peak temperature. DSC measurements were made at a heating rate of 10° C. in a pierced pan in air.

TABLE 3

Melting points of monohydrate lisinoprils

| Monohydrate form I | | Monohydrate form 2 | |
|---|---|---|---|
| Onset/° C. | Peak/° C. | Onset/° C. | Peak/° C. |
| 174.8 | 185.1 | 167.4 | 177.1 |

The difference in melting points of the two monohydrates clearly indicates that they are different polymorphs and that the difference in XRPD was not simply a consequence of preferred orientation of the crystals on the sample holder (a phenomenon known as "preferred orientation").

The water content of the monohydrates was determined by TGA using a Mettler Toledo TGA851 instrument, and Karl-Fischer analysis. Both monohydrate forms were found to have water contents of about 4% (the theoretical water content of a monohydrate of lisinopril is 4.08% by weight), indicating that they are indeed monohydrates.

Spectroscopic Analysis

Raman analysis was carried out with no prior sample preparation; the samples were placed in vials and held in the path of the laser beam for measurement. Low laser powers were used to ensure no sample damage, and the spectra showed no evidence of sample heating. Errors in band position measurement are of the order of 1–2 $cm^{-1}$ due to digitisation noise.

IR measurements were made with no sample preparation to ensure that no change of polymorph could take place. The samples were placed on the surface of a diamond window and transmission measurements were made using an IR microscope.

Raman and IR spectroscopy show clear differences in the spectra of the two forms of monohydrate.

TABLE 4

Raman Spectroscopy-characteristic bands of the two monohydrate forms.
Peak positions are measured in $cm^{-1}$

| Monohydrate form 1 | Monohydrate form 2 |
|---|---|
| 3070 | absent |
| 3061 | 3061 |
| 3050 | 3050 |
| 3042 | 3042 |
| 2988 | 2988 |
| 2966 | absent |
| 2937 | 2937 |
| 2900 | 2900 |
| 2870 | absent |
| 1652 | 1651 |
| 1604 | absent |
| 1600 | 1600 |
| 1585 | absent |
| 1581 | 1580 |
| 1375 | 1375 |
| 1196 (weak) | 1196 (strong) |
| 1002 | 1001 |
| 834 (weak) | 834 (strong) |

Differences in the Raman spectra of the two monohydrates include an additional band in the 3020–3080 region of monohydrate form 1. Both monohydrates have bands at 3042, 3051 and 3061 $cm^{-1}$ and monohydrate form 1 has a band at 3070 $cm^{-1}$. Monohydrate form 1 has bands at 2966 and 2870 $cm^{-1}$, attributed to aliphatic C-H stretching, which are absent in monohydrate form 2. Monohydrate form 1 has bands at 1580, 1585, 1600 and 1604 $cm^{-1}$, while monohydrate form 2 has only two bands, at 1580 and 1600 $cm^{-1}$ in this region. There are two bands, which are strong in monohydrate form 2 and weak in monohydrate form 1, at 1196 and 834 $cm^{-1}$.

TABLE 5

Characteristic IR absorbances for monohydrates 1 and 2 (Units are $cm^{-1}$)

| Monohydrate form 1 | Monohydrate form 2 |
|---|---|
| 3640 | 3637 |
| 3440 | 3440 |
| 3407 | Absent |
| 3293 | Absent |
| 1653 | 1648 |
| 1621 | 1617 |
| 1577 | 1564 |
| 1451 | 1451 |
| 1443 | 1443 |
| 1373 | 1373 |
| 1205 | 1205 |
| 761 | 759 |
| 708 | 705 |

Differences between the two monohydrates are seen in the IR spectrum. The IR absorbance due to free hydroxyl (OH) occurs at 3640 $cm^{-1}$ for monohydrate form 1 and at 3637 $cm^{-1}$ for monohydrate form 2. Monohydrate form 1 has absorbances at 3440, 3407 and 3293 $cm^{-1}$ due to hydrogen-bonded OH while monohydrate form 2 has a weaker absorbance at 3440 $cm^{-1}$ only. Band shifts occur in other parts of the IR absorption spectrum: monohydrate form 1 has absorbances at 1653, 1621 and 1577 $cm^{-1}$ and monohydrate form 2 has corresponding absorbances at 1648, 1617 and 1564 $cm^{-1}$.

Microscopic analysis also identified differences between the two monohydrate forms of lisinopril prepared according to Example 1.

SEM showed that monohydrate form 1 consisted of long needles 50 to 500 $\mu$m in length. In contrast, the crystals of monohydrate form 2 are much smaller, and in a narrower size range, than those of monohydrate form 1, typically 5 $\mu$m or less in edge length.

Solubility

The solubility of monohydrate lisinopril form 2 was measured visually. It has a solubility of about 400–450 mg/ml. The reference solubility of lisinopril dihydrate is 97 mg/ml (Ip et al., ibid, page 252). The much greater solubility of the novel monohydrate lisinopril form 2 over the dihydrate makes the former preferable for the manufacture of a fast melt formulation.

Summary of Characterising Features of Monohydrate Form 2 and Differences From Monohydrate Form 1 (Corresponding to the Monohydrate Disclosed by Ip et al.).

Monohydrate lisinopril form 2 has major characteristic X-ray diffraction peaks at d-spacings of about 12.0, 11.5, 7.6, 6.5, 5.4, 4.59, 4.52, 4.23, 4.16, 4.09, 3.91, 3.75, 3.71 and 3.29Å. This list comprises the most intense 11 peaks and the three distinctive, though weaker, peaks at 4.52, 3.75 and 3.71 Å.

It can be distinguished from monohydrate form 1 and the monohydrate disclosed by Ip et al by the presence of peaks at d-spacings of 12.0, 4.52, 3.75 and 3.71 Å and/or by the absence of peaks at d-spacings of 15.2, 8.1, 6.3, 5.69 and 4.72Å. On close inspection, peaks at d-spacings of 6.9, 5.92, 5.09, 4.99, 3.33 and 2.96 Å are also missing.

With monohydrate lisinopril form 2 melt onset occurs at about 167° C. and the peak of the endotherm occurs at about 177° C. when measured by DSC at a heating rate of 10° C./min in a pierced pan in air. Monohydrate lisinopril form 1 has melt onset occurs at about 175° C. and the peak of the endotherm occurs at about 185° C.

Monohydrate lisinopril form 2 has characteristic IR absorption bands at 3637, 3440, 1648, 1617, 1564, 1451, 1443, 1373, 1205, 759 and 705 cm$^{-1}$. It can be distinguished from monohydrate lisinopril form 1 by the absence of absorbances at 3407 and 3293 cm$^{-1}$.

Monohydrate lisinopril form 2 has characteristic Raman bands at 3061, 3050, 3042, 2988, 2937, 2900, 1651, 1600, 1580, 1375, 1196, 1001 and 834 cm$^{-1}$. It can be distinguished from monohydrate lisinopril form 1 by the absence of peaks at 3070, 2966, 2870, 1604 and 1585 cm$^{-1}$.

What is claimed is:

1. A method of inhibiting angiotensin converting enzyme comprising administering to a subject suffering from hypertension, congestive heart failure, acute myocardial infarction or renal or retinal complications of diabetes mellitus a composition comprising a lisinopril monohydrate formed by the process consisting of:
    (a) dissolving lisinopril (1-(N$^2$-[(S)-1-carboxy-3-phenylpropyl]-L-lysyl)-L-proline) in water to form a solution;
    (b) adding isobutanol to the solution of step (a) in an amount and under conditions effective to induce crystallisation of the lisinopril;
    (c) isolating the crystals formed in step (b);
    (d) drying the crystals at a temperature not to exceed 80° C. for a time and under conditions effective to produce particulate crystalline lisinopril monohydrate; and
    (e) recovering the crystalline lisinopril monohydrate, wherein the administration is for a time and under conditions effective to inhibit angiotensin converting enzyme.

2. The method of claim 1, wherein the composition is a fast melt tablet.

3. The method of claim 1, wherein the subject is suffering from hypertension.

4. The method of claim 3, wherein the composition is a fast melt tablet.

5. The method of claim 1, wherein the subject is suffering from congestive heart failure.

6. The method of claim 5, wherein the composition is a fast melt tablet.

7. A method of inhibiting angiotensin converting enzyme comprising administering to a subject suffering from hypertension, congestive heart failure, acute myocardial infarction or renal or retinal complications of diabetes mellitus a composition comprising a particulate crystalline lisinopril (1-(N$^2$-[(S)-1-carboxy-3-phenylpropyl]-L-lysyl)-L-proline) monohydrate characterized in having an X-ray diffraction pattern comprising strong or very strong peaks at d-spacings of 12.0 and 11.5Å for a time and under conditions effective to inhibit angiotensin converting enzyme.

8. The method of claim 7, wherein the composition is a fast melt tablet.

9. The method of claim 7, wherein the subject is suffering from hypertension.

10. The method of claim 9, wherein the composition is a fast melt tablet.

11. The method of claim 7, wherein the subject is suffering from congestive heart failure.

12. The method of claim 11, wherein the composition is a fast melt tablet.

13. A method of treating hypertension comprising administering to a subject in need thereof a composition comprising crystalline lisinopril monohydrate for a time and under conditions effective to ameliorate said hypertension, wherein said crystalline lisinopril monohydrate is formed by a process consisting of:
    (a) dissolving lisinopril (1-(N$^2$-[(S)- 1-carboxy-3-phenylpropyl]-L-lysyl)-L-proline) in
    (b) adding isobutanol to the solution of step (a) in an amount and under conditions effective to induce crystallization of the lisinopril;
    (c) isolating the crystals formed in step (b);
    (d) drying the crystals at a temperature not to exceed 80° C. for a time and under conditions effective to produce particulate crystalline lisinopril monohydrate; and
    (e) recovering the crystalline lisinopril monohydrate.

14. The method of claim 13 wherein said composition is a fast melt tablet.

* * * * *

UNITED STATES PATENT AND TRADEMARK OFFICE
CERTIFICATE OF CORRECTION

PATENT NO.     : 6,468,976 B1
DATED          : October 22, 2002
INVENTOR(S)    : John Brown It is certified that error appears in the above-identified patent and that said Letters Patent is hereby corrected as shown below:

<u>Column 13,</u>
Line 25, replace "composition comprising a lisinopril" with
-- composition comprising crystalline lisinopril --.

<u>Column 14,</u>
Line 34, please add -- water to form a solution; -- after "in".

Signed and Sealed this

Eleventh Day of February, 2003

JAMES E. ROGAN
*Director of the United States Patent and Trademark Office*